United States Patent [19]

Buschmann et al.

[11] Patent Number: 4,472,412

[45] Date of Patent: Sep. 18, 1984

[54] CONTROL OF FUNGI USING PHENYLPROPYLAMMONIUM SALTS

[75] Inventors: Ernst Buschmann; Bernd Zeeh, both of Ludwigshafen; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 410,877

[22] Filed: Aug. 24, 1982

[30] Foreign Application Priority Data

Aug. 29, 1981 [DE] Fed. Rep. of Germany ....... 3134220
Sep. 9, 1981 [DE] Fed. Rep. of Germany ....... 3135592

[51] Int. Cl.$^3$ .................. A61K 31/445; C07D 211/14
[52] U.S. Cl. .................... 424/267; 548/578; 260/239 B; 260/239 BF; 544/58.1; 544/59; 544/173; 544/174; 544/175; 546/216; 546/219; 546/220; 546/221; 546/222; 546/192; 424/244; 424/246; 424/248.4
[58] Field of Search .................. 542/466; 544/58.1, 59, 544/178, 106; 424/267, 274, 246, 244, 248.4; 260/239 B, 239 BF; 546/192, 216; 548/578

[56] References Cited

U.S. PATENT DOCUMENTS

| 2,842,546 | 7/1958 | Lane | 260/247 |
| 3,037,910 | 6/1962 | Copp et al. | 167/65 |
| 4,241,058 | 12/1980 | Pfiffner | 424/248.4 |

FOREIGN PATENT DOCUMENTS

| 7479 | 7/1977 | European Pat. Off. | 546/192 |
| 2604 | 12/1978 | European Pat. Off. | 546/192 |
| 31114 | 12/1980 | European Pat. Off. | 546/192 |
| 1591267 | 6/1971 | United Kingdom | 546/192 |

OTHER PUBLICATIONS

Fieser and Fieser, "Organic Chemistry", 3rd Edition, (1956), (Heath), p. 228.
Stanier et al., "The Microbial World", (1957), (Prentice-Hall), Chapter 5, pp. 76–98.
Chemical Week, Jun. 21, 1972, p. 46.
Wegler, Chemie der Pflanzenschutzund Schädlingsbekämpfungsmittel, vol. 4, (1977), pp. 24–26.

*Primary Examiner*—Robert T. Bond
*Attorney, Agent, or Firm*—Keil & Weinkauf

[57] ABSTRACT

A fungicidal agent contains a phenylpropylammonium salt of the formula

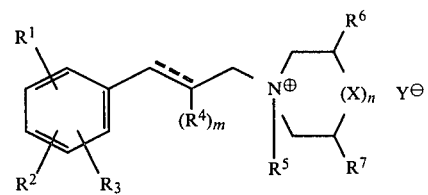

where $R^1$, $R^2$ and $R^3$ are each hydrogen, unsubstituted or substituted alkyl, unsubstituted or substituted aryl or aralkyl, cycloalkyl, alkoxy, acyl or halogen, $R^4$ is alkyl, alkenyl or alkoxy, $R^5$ is alkyl, alkenyl, alkynyl or unsubstituted or substituted aralkyl, $R^6$ and $R^7$ are each hydrogen, alkyl, $CH_2OH$ or OH, X is $CH_2$, O, S, C=O, $(CH_2)_2$ or $CH_2CH$—$R^8$ where $R^8$ is alkyl, m is 0, 1 or 2, n is 0 or 1 and $Y^\ominus$ is the anion of a non-phytotoxic acid, with the proviso that the bond represented by the broken line may be hydrogenated if m is 0 or 1, and is always hydrogenated if m is 2.

1 Claim, No Drawings

CONTROL OF FUNGI USING PHENYLPROPYLAMMONIUM SALTS

The present invention relates to fungicides which contain quaternary phenylpropylammonium salts, and a process for controlling fungi with these compounds.

The use of N-trichloromethylthiotetrahydrophthalimide as a fungicide has been disclosed (Chemical Week, June 21, 1972, page 46).

We have found that phenylpropylammonium salts of the formula

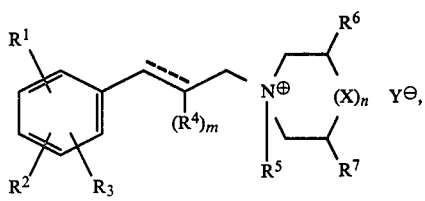

where $R^1$, $R^2$ and $R^3$ independently of one another are each hydrogen, unsubstituted or halogen-substituted alkyl, unsubstituted or substituted aryl or aralkyl, cycloalkyl, alkoxy, acyl or halogen, $R^4$ is alkyl, alkenyl or alkoxy, $R^5$ is alkyl, alkenyl, alkynyl or unsubstituted or substituted aralkyl, $R^6$ and $R^7$ independently of one another are each hydrogen, alkyl, $CH_2OH$ or OH, X is $CH_2$, O, S, C=O, $(CH_2)_2$ or $CH_2CH-R^8$ where $R^8$ is alkyl, m is 0, 1 or 2, n=0 or 1 and $Y^\ominus$ is the anion of a non-phytotoxic acid, with the proviso that the bond represented by the broken line may be hydrogenated if m is 0 or 1, and is always hydrogenated if m is 2, possess good fungicidal activity.

$R^1$, $R^2$ and $R^3$ are each, for example, $C_1$–$C_8$-alkyl, methyl, ethyl, n-propyl, isopropyl, n-butyl, isobutyl, tert.-butyl, n-pentyl, tert.-amyl, 1,1-dimethylbutyl, 1,1-dimethylpentyl, 1,1-dimethylhexyl, 1,1-diethylethyl, 1,1,2-trimethylpropyl, $C_1$–$C_4$-haloalkyl, 2-chloro-1,1-dimethylethyl, 2-fluoro-1,1-dimethylethyl, 2-bromo-1,1-dimethylethyl, trichloromethyl, trifluoromethyl, $C_3$–$C_7$-cycloalkyl, cyclopropyl, cyclopentyl, cyclohexyl, cycloheptyl, phenyl, halophenyl, $C_1$–$C_4$-alkylphenyl, 4-tert.-butylphenyl, 4-chlorophenyl, benzyl, halobenzyl, 4-chlorobenzyl, 2,4,6-trimethylbenzyl, phenylethyl, 4-chlorophenylethyl, 4-tert.-butylphenylethyl, 2-phenylpropyl, 2-(p-tert.-butylphenyl)-propyl, 2-(4-chlorophenyl)-propyl, 2-(2,4-dichlorophenyl)-propyl, $C_1$–$C_4$-alkoxy, methoxy, ethoxy, tert.-butoxy, $C_2$–$C_4$-alkanoyl, acetyl, propionyl, butyryl, benzoyl, fluorine, chlorine, bromine, iodine or hydrogen.

$R^4$ is, for example, $C_1$–$C_6$-alkyl, methyl, ethyl, n-propyl, isopropyl, n-butyl, isobutyl, tert.-butyl, n-pentyl, n-hexyl, $C_3$–$C_4$-alkenyl, propen-1-yl, buten-1-yl, $C_1$–$C_3$-alkoxy, methoxy, ethoxy or propoxy.

$R^5$ is, for example, $C_1$–$C_4$-alkyl, methyl, ethyl, n-propyl, n-butyl, isobutyl, $C_2$–$C_4$-alkenyl, allyl, 2-butenyl, 2-methylallyl, propargyl, crotyl, benzyl, halobenzyl, 4-chlorobenzyl, 4-fluorobenzyl, 4-bromobenzyl, 4-cyanobenzyl, 4-nitrobenzyl, 4-$CF_3$-benzyl, 4-iodobenzyl, $C_1$–$C_4$-alkylbenzyl, 4-methylbenzyl, 4-tert.-butylbenzyl, 2,4-dichlorobenzyl, 2,6-dichlorobenzyl, 2,3,6-trichlorobenzyl, 2,3,4-trichlorobenzyl or 3,4-dichlorobenzyl.

$R^6$ and $R^7$ are each, for example, hydrogen, methyl, ethyl, propyl, $CH_2OH$ or OH.

$Y^\ominus$ is, for example, $Cl^\ominus$, $Br^\ominus$, $I^\ominus$, $NO_3^\ominus$, ½ $(SO_4^{2-})$ or $CH_3C_6H_5SO_3^\ominus$.

Where a double bond is adjacent to the aromatic ring, this bond may exhibit either a Z or an E configuration. $R^6$ and $R^7$ may be cis or trans to one another. The fungicidal agents may also contain these isomers.

The above phenylpropylammonium salts are active ingredients in fungicides, and have a good fungicidal action.

Some of the phenylpropylammonium salts have been disclosed in German Laid-Open Application DOS No. 2,952,382.

Compounds which have not yet been described are readily obtainable from phenylpropylamines of the formula

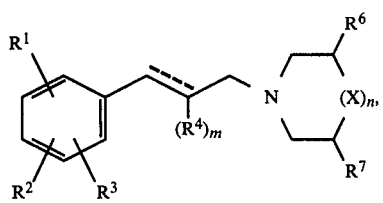

where $R^1$, $R^2$, $R^3$, $R^4$, $R^6$, $R^7$ m, n and X have the above meanings, some of these compounds having been disclosed in German Laid-Open Application DOS No. 2,752,096. The end compounds may be obtained by reacting such a tertiary amine with a quaternizing agent $R^5Y$. Examples of suitable quaternizing agents are, in addition to the alkyl, alkenyl and alkynyl ($R^5$) halides, dimethyl sulfate, diethyl sulfate, and sulfonates of the formula $RSO_3R^5$ where R may be $C_1$–$C_7$-alkyl, or aralkyl or phenyl which is substituted by halogen or by alkyl.

Alternatively, the novel quaternary ammonium salts may be prepared by reacting an amine of the formula

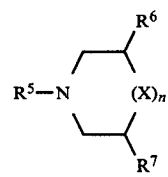

with a phenylpropyl halide of the formula

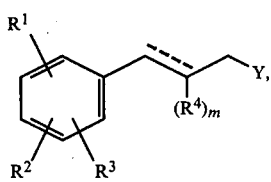

where $R^1$, $R^2$, $R^3$, $R^4$, $R^5$, $R^6$, $R^7$, X, n and m have the above meanings and Y is Cl, Br or I, some of which have been disclosed in German Laid-Open Application DOS No. 2,752,096.

The equation which follows illustrates the preparation of compounds of the formulae II and III by conventional reactions.

The preparation of the aldehyde IV is described by B. Zeeh and E. Buschmann in Liebig's Ann. Chem. 1979, page 1585.

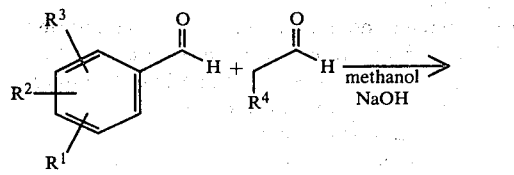
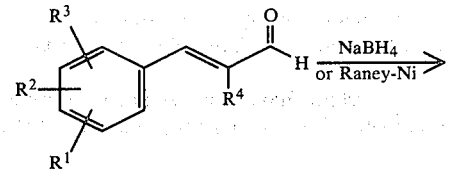
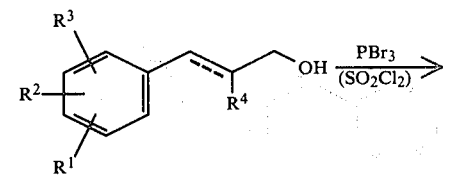
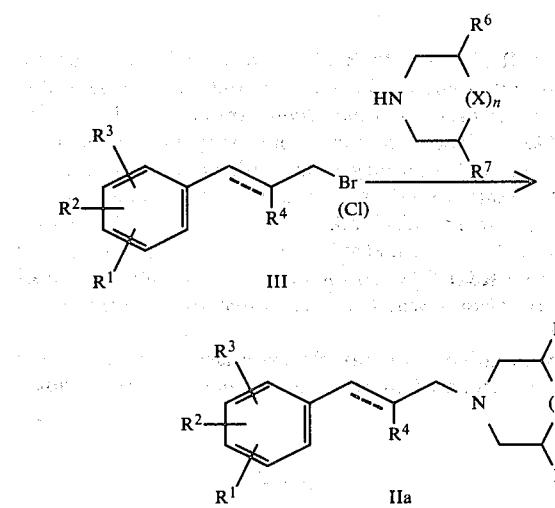
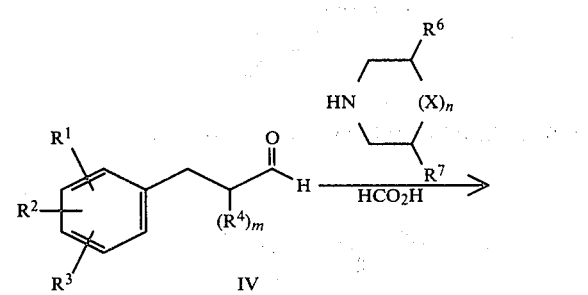
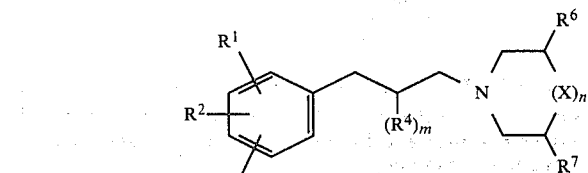
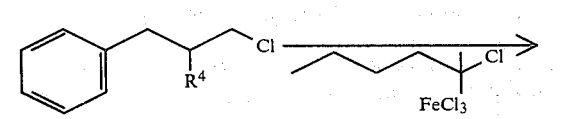
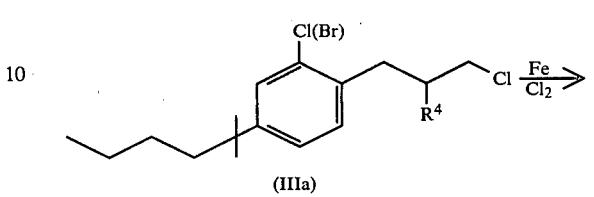
(IIIa)
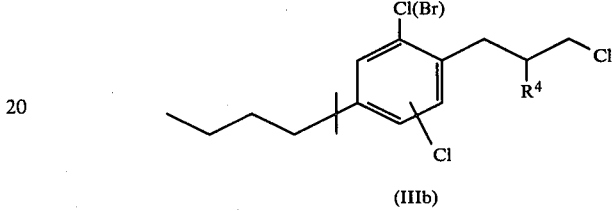
(IIIb)
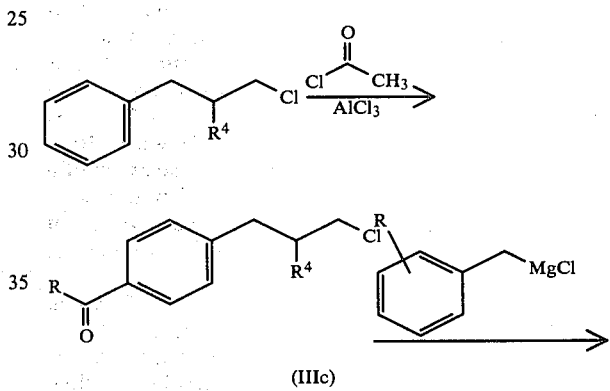
(IIIc)
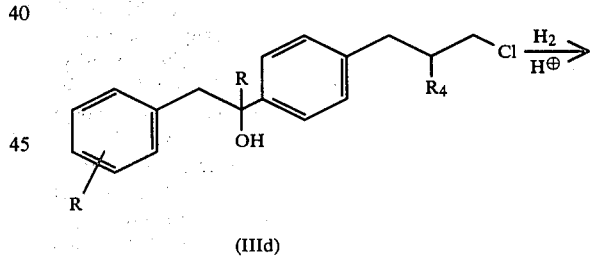
(IIId)
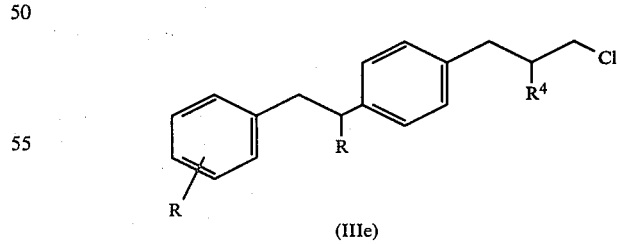
(IIIe)
The phenylpropylammonium salts are obtained by reacting a phenylpropylamine of the formula II with an alkylating agent of the formula $R^5Y$, where $R^5$ and Y have the above meanings.
Alternatively, the active ingredients may be obtained by reacting a phenylpropyl halide of the formula III with a tertiary amine of the formula V

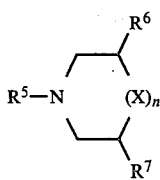

where $R^5$, $R^6$, $R^7$, X and n have the above meanings.

The reactions of the phenylpropylamine II with $R^5Y$ and of the phenylpropyl halide III with the tertiary amine V are carried out, for example, at from 10° to 150° C., in the presence or absence of a solvent, eg. ethanol, methanol, $CHCl_3$, $CH_2Cl_2$, acetone, cyclohexanone, tetrahydrofuran, acetonitrile, dimethylformamide or ethyl acetate, under atmospheric or superatmospheric pressure.

The Examples which follow illustrate the preparation of the compounds.

EXAMPLE 1

(a) 2-n-Pentyl-3-(2,4-dichlorophenyl)-acrolein (I)

342 g of heptanal were added dropwise to a solution of 525 g of 2,4-dichlorobenzaldehyde and 12 g of NaOH in 1.5 l of methanol in the course of 6 hours. The mixture was allowed to continue reacting for 1 hour, then acidified with glacial acetic acid, and concentrated after a further 15 hours. The residue was taken up in $CH_2Cl_2/H_2O$, and the organic phase was washed with water, dried over $Na_2SO_4$ and concentrated. Distillation of the residue gave 498 g of (I) of boiling point 152°–160° C./0.2 mbar.

(b) 2-n-Pentyl-3-(2,4-dichlorophenyl)-allyl alcohol (II)

54.5 g of $NaBH_4$ were added, in portions, to a solution of 150 g of (I) in 1.5 l of methanol. The mixture was refluxed for 1 hour and then concentrated, 1 l of 2N HCl was added, and the mixture was refluxed for a further hour and then extracted with $CH_2Cl_2$. The organic phase was washed with water, dried over $Na_2SO_4$ and concentrated. Distillation of the residue gave 93 g of (II) of boiling point 156°–160° C./0.2 mbar.

(c) 2-n-Pentyl-3-(2,4-dichlorophenyl)-allyl bromide (III)

32.5 g of $PBr_3$ were added dropwise to a solution of 93 g of (II) in 300 ml of $CHCl_3$ at 10° C. The $CHCl_3$ solution was stirred for 15 hours at room temperature and then poured into ice/water. The organic phase was separated off and the aqueous phase was extracted with $CHCl_3$. The combined organic phases were washed several times with aqueous $Na_2CO_3$ solution and with water, dried over $Na_2SO_4$ and concentrated. Distillation of the residue gave 110 g of (III) of boiling point 140°–148° C./0.1 mbar.

(d) N-[2-n-Pentyl-3-(2,4-dichlorophenyl)-prop-2-en-1-yl]-pyrrolidine (IV)

A mixture of 50 g of (III) and 31.7 g of pyrrolidine was heated for 5 hours at 150° C. in an oil bath. The crude product was cooled, and dissolved in $CHCl_3$, and the solution was washed with dilute NaOH and then several times with water. The organic phase was dried over $Na_2SO_4$ and concentrated. Distillation of the residue gave 19 g of (IV) of boiling point 148°–150° C./0.1 mbar.

(e) N-[2-n-Pentyl-3-(2,4-dichlorophenyl)-prop-2-en-1-yl]-N-allyl-pyrrolidinium bromide (V)

19 g of (IV) and 14.5 g of allyl bromide in 200 ml of glacial acetic acid were refluxed for 5 hours, the mixture was cooled, and the liquid product which separated out was triturated with ethyl acetate. The product which crystallized out was filtered off under suction, washed with ethyl acetate and dried under reduced pressure. 14 g of (V) of melting point 109° C. were obtained (compound No. 3a).

EXAMPLE 2

(a) 1-[4-tert.-butylphenyl]-2-[4-(3-chloro-2-methylpropyl)-phenyl]-propan-2-ol (VI)

168.4 g of 3-(4-acetylphenyl)-2-methylpropyl chloride in 100 ml of diethyl ether were added dropwise to a Grignard suspension prepared from 182.5 g of 4-tert.-butylbenzyl chloride and 26 g of Mg in 400 ml of diethyl ether. After completion of the dropwise addition, the mixture was refluxed for a further 2 hours and then hydrolyzed by adding ice-cooled dilute aqueous HCl until the pH was 2. The organic products were extracted with ether, and the organic phase was washed with water, dried over $Na_2SO_4$ and concentrated. Distillation of the residue gave 163.4 g of (VI) of boiling point 190° C./0.1 mbar.

(b) N-{3-[4-(1-(4-t-butylphenyl)-propan-2-ol-2-yl)-phenyl]-2-methyl-propyl}-2,6-cis-dimethylmorpholine (VII)

A mixture of 164 g of (VI) and 159 g of 2,6-cis-dimethylmorpholine was stirred for 6 hours at 150° C. The crude product was dissolved in $CHCl_3$, and the solution was washed with dilute aqueous NaOH and then with water, dried over $Na_2SO_4$ and concentrated. Distillation of the residue gave a yield of 147 g of (VII) of boiling point 214°–218° C./0.3 mbar.

(c) N-{3-[4-(1-(4-t-butylphenyl)-propan-2-yl)-phenyl]-2-methyl-propyl}-2,6-cis-dimethylmorpholine (VIII)

A solution of 50 g of (VII) in 1 l of glacial acetic acid and 30 ml of concentrated $H_2SO_4$ was hydrogenated in the presence of 5 g of 5% strength Pd/C at room temperature and under 5 bar, until the pressure remained constant. The catalyst was filtered off and the filtrate was made alkaline with dilute aqueous NaOH. The crude product was extracted with $CH_2Cl$, and the solution was washed with $H_2O$, dried over $Na_2SO_4$ and concentrated. Distillation of the residue gave 40 g of product of boiling point 200°–202° C./0.3 mbar.

(d) N-{3-[4-(1-4-t-butylphenyl)-propan-2-yl]-phenyl-2-methyl-propyl}-N-methyl-2,6-cis-dimethyl-morpholinium bromide (IX)

42 g of (VIII) in 200 ml of $CH_3CN$ were added to a solution of 38 g of $CH_3Br$ in 200 ml of $CH_3CN$ and, after 15 hours at room temperature, the mixture was concentrated. The residue crystallized on trituration with ether. The product was filtered off under suction, washed with ether and dried under reduced pressure. 36 g of product of melting point 210° C. (decomposition) were obtained (compound No. 65).

EXAMPLE 3

(a) N-[3-(2,4-dichlorophenyl)-2-methyl-2-(prop-2-en-1-yl)-propyl]-pyrrolidine (X)

149 g of formic acid were added dropwise to 45.8 g of pyrrolidine, while cooling with ice. 181 g of 3-(2,4-dichlorophenyl)-2-methyl-2-propen-1-ylpropionaldehyde were then added, after which the mixture was heated at 100° C. for 12 hours and then evaporated down under reduced pressure. The residue was made alkaline with 25% strength NaOH and extracted with ether, and the organic phase was dried over KOH and evaporated down. Distillation of the residue gave 95 g of (X) of boiling point 130°–138° C./0.1 mbar.

(b) N-Allyl-N-[3-(2,4-dichlorophenyl)-2-methyl-2-(prop-2-en-1-yl)-propyl]-pyrrolidinium bromide A solution of 40 g of (X) and 31.5 g of allyl bromide in 300 ml of ethyl acetate was refluxed for 5 hours. The precipitated product was filtered off under suction, washed with ethyl acetate and dried under reduced pressure. Yield: 15 g; melting point: 174° C. (compound No. 56).

EXAMPLE 4

(a) 3-[4-(1,1-dimethylpentyl)-phenyl]-2-methylpropyl chloride (XII)

342 g of 1,1-dimethylpentyl chloride were added dropwise to a mixture of 428 g of 3-phenyl-2-methylpropyl chloride and 40.6 g of $FeCl_3$ at 35° C., and the mixture was stirred for 7 hours at 50° C. and for 14 hours at room temperature. The crude product was dissolved in 2 l of $CHCl_3$, and the solution was washed with dilute HCl and water, dried over $Na_2CO_3$ and concentrated. Distillation of the residue gave 500 g of (XII) of boiling point 126°–132° C./0.2 mbar.

(b) 3-[2-Bromo-4-(1,1-dimethyl-pentyl)-phenyl]-2-methylpropyl chloride (XIII)

180 g of $Br_2$ were added dropwise to a mixture of 300 g of XII and 3 g of Fe powder at room temperature, and the mixture was stirred for 14 hours at room temperature. The crude product was dissolved in $CH_2Cl_2$, and the solution was washed with water, dried over $Na_2SO_4$ and distilled. 220 g of (XIII) of boiling point 160° C./0.1 mbar were obtained.

(c) N-{3-[2-Bromo-4-(1,1-dimethylpentyl)-phenyl]-2-methylpropyl}-piperidine (XIV)

A mixture of 50 g of XIII and 38.3 g of piperidine was heated at 150° C. for 7 hours. The mixture was cooled and then taken up in $CHCl_3$, and the solution was washed with dilute NaOH and then with water, dried over $Na_2SO_4$ and concentrated. Distillation of the residue gave 27 g of (XIV) of boiling point 170°–171° C./0.1 mbar.

(d) N-{3-[2-Bromo-4-(1,1-dimethylpentyl)-phenyl]-2-methylpropyl}-N-methyl-piperidinium bromide (XV)

17 g of (XIV) in 100 ml of $CH_3CN$ were added to a solution of 16.4 g of $CH_3Br$ in 200 ml of $CH_3CN$. After 14 hours at room temperature, the mixture was concentrated. The crystalline residue was triturated with ether, filtered off under suction and dried under reduced pressure. Yield: 15 g; melting point: 178° C. (compound No. 78).

EXAMPLE 5

(a) 3-[2,6-dichloro-4-(1,1-dimethylpentyl)-phenyl]-2-methylpropyl chloride (XVI)

178 g of $Cl_2$ gas were passed into a solution of 4 g of Fe powder in 500 g of (XII) 10°–30° C. The formation of the initially monochlorinated and subsequently dichlorinated product was followed by means of gas chromatography. An additional amount of $Cl_2$ was passed in when necessary. The crude product was taken up in $CH_2Cl_2$, and the solution was washed with water, dried over $Na_2SO_4$ and distilled. 390 g of (XVI) of boiling point 152° C./0.1 mbar were obtained.

The isomeric 2,5- and 2,3-dichlorophenyl compounds were formed as by-products in the above chlorination.

(b) N-{3-[2,6-dichloro-4-(1,1-dimethylpentyl)-phenyl]-2-methylpropyl}-piperidine (XVII)

The product was obtained from 150 g of (XVI) and 115 g of piperidine, by a method similar to that described in Example 4c. Yield: 125 g; boiling point: 177°–185° C./0.3 mbar.

The 2,3- and 2,5-dichlorophenyl compounds were formed as by-products in the preparation of the above piperidine derivative (see Example 5a).

(c) N-{3-[2,6-dichloro-4-(1,1-dimethylpentyl)-phenyl]-2-methylpropyl}-N-(4-$CF_3$-benzyl)-piperidinium bromide (XVIII)

A solution of 17 g of (XVII) and 17.9 g of p-$CF_3$-benzyl bromide in 300 ml of ethyl acetate was refluxed for 6 hours and then cooled. The precipitated product was filtered off under suction, washed with ethyl acetate and dried under reduced pressure. Yield: 2 g; melting point: 206° C. When the mother liquor was concentrated, the residue triturated with ethyl acetate, and the product filtered off under suction, washed and dried, a further 16 g of (XVIII) of melting point 204° C. were obtained (compound No. 86).

The corresponding 2,3- and 2,5-dichloro compounds were formed as by-products in the preparation of the above salt (see Example 5b).

EXAMPLE 6

(a) 2-n-Butyl 3-(2,3,4-trichlorophenyl)-acrolein (XIX)

The product is obtained from 266 g of 2,3,4-trichlorobenzaldehyde and 127 g of hexanal, by the method described in Example 1a. Yield: 210 g; melting point: 181°–182° C./0.2 mbar.

(b) 2-n-Butyl-3-(2,3,4-trichlorophenyl)-propan-1-ol (XX)

A suspension of 60 g of Raney nickel in 435 g of (XIX) and 1 l of methanol was flushed with nitrogen and then hydrogenated in an autoclave, at 60°–70° C. and under 100 bar, until the pressure remained constant. The catalyst was filtered off under suction, and the filtrate was concentrated and distilled, giving 278 g of (XX) of boiling point 167° C./0.1 mbar.

(c) 2-n-Butyl-3-(2,3,4-trichlorophenyl)-propyl chloride (XXI)

332 g of (XX) were added dropwise to 148 g of thionyl chloride, and the mixture was stirred for 14 hours at room temperature and for 2 hours at 140° C. Distillation gave 278 g of (XXI) of boiling point 142°-145° C./0.1 mbar.

(d)
N-[2-n-Butyl-3-(2,3,4-trichlorophenyl)-propyl]-pyrrolidine (XXII)

The product was obtained from 140 g of (XXI) and 95 g of pyrrolidine, by a method similar to that described in Example 4c. Yield: 135 g; boiling point: 166°-167° C./0.1 mbar.

(e)
N-Allyl-N-[2-n-butyl-3-(2,3,4-trichlorophenyl)-propyl]-pyrrolidinium bromide (XXIII)

A solution of 34.8 g of (XXII) and 36.3 g of allyl bromide in 250 ml of ethyl acetate was refluxed for 5 hours. The product, which was obtained as an oil, was washed several times with ethyl acetate and then freed from residual solvent under reduced pressure. Yield: 32 g of a yellowish brown resin (compound No. 60).

The compounds below were prepared in a corresponding manner.

| No. | $R^1$ | $R^2$ | $R^3$ | $R^4$ | $R^5$ | $R^6$ | $R^7$ | $(X)_n$ | Y | M.p. °C. |
|---|---|---|---|---|---|---|---|---|---|---|
| 1a | 2-Cl | 4-Cl | H | $CH_3$ | allyl | H | H | — | Br | 110 |
| 2a | 2-Cl | 4-Cl | H | n-pentyl | allyl | H | H | $CH_2$ | Br | 148 |
| 3a | 2-Cl | 4-Cl | H | n-pentyl | allyl | H | H | — | Br | 109 |
| 4a | 2-Cl | 4-Cl | H | iso-propyl | allyl | H | H | — | Br | 75 |

| No. | $R^1$ | $R^2$ | $R^3$ | $(R^4)_m$ | $R^5$ | $R^6$ | $R^7$ | $(X)_n$ | Y | M.p. °C. |
|---|---|---|---|---|---|---|---|---|---|---|
| 1 | 4-t-Bu (tert.)-butyl) | H | H | $CH_3$ | allyl | H | H | CH—tBuCH$_2$ | Br | 153 |
| 2 | 4-CH(CH$_3$)$_2$ | H | H | $CH_3$ | allyl | H | H | CHtBuCH$_2$ | Br | 152 |
| 3 | 4-t-Bu | H | H | $CH_3$ | $CH_3$ | H | H | CHtBuCH$_2$ | Br | 216 |
| 4 | 4-CH(CH$_3$)$_2$ | H | H | $CH_3$ | $CH_3$ | H | H | CHtBuCH$_2$ | Br | 190 |
| 5 | 4-t-Bu | H | H | $CH_3$ | $CH_3$ | $CH_3$ | $CH_3$ | O | Br | 184 |
| 6 | 4-t-Bu | H | H | $CH_3$ | propargyl | $CH_3$ | $CH_3$ | O | Br | 82 |
| 7 | 4-t-Bu | H | H | $CH_3$ | allyl | $CH_3$ | $CH_3$ | O | Br | 61 |
| 8 | 4-t-Bu | H | H | $CH_3$ | ethyl | $CH_3$ | $CH_3$ | O | $C_2H_5SO_4^\ominus$ | 85 |
| 9 | 4-t-Bu | H | H | $CH_3$ | $CH_3$ | $CH_3$ | $CH_3$ | $CH_2$ | Br | 220 |
| 10 | 4-t-Bu | H | H | $CH_3$ | $C_2H_5$ | $CH_3$ | $CH_3$ | $CH_2$ | Br | 197 |
| 11 | 4-t-Bu | H | H | $CH_3$ | allyl | $CH_3$ | $CH_3$ | $CH_2$ | Br | 80 |
| 12 | 4-t-Bu | H | H | $CH_3$ | benzyl | $CH_3$ | $CH_3$ | $CH_2$ | Br | 224 |
| 13 | 4-t-Bu | H | H | $CH_3$ | 4-Cl—benzyl | $CH_3$ | $CH_3$ | $CH_2$ | Br | 187 |
| 14 | 4-t-Bu | H | H | $CH_3$ | 4-F—benzyl | $CH_3$ | $CH_3$ | $CH_2$ | Br | 209 |
| 15 | 4-t-Bu | H | H | $CH_3$ | $CH_3$ | $CH_3$ | $CH_3$ | O | $CH_3SO_4^\ominus$ | 130 |
| 16 | 4-t-Bu | H | H | $CH_3$ | $C_2H_5$ | $CH_3$ | $CH_3$ | O | $C_2H_5SO_4^\ominus$ | 72 |
| 17 | 4-t-Bu | H | H | $CH_3$ | benzyl | $CH_3$ | $CH_3$ | O | Br | 196 |
| 18 | 4-t-Bu | H | H | $CH_3$ | 4-Br—benzyl | $CH_3$ | $CH_3$ | O | Br | 198 |
| 19 | 4-t-Bu | H | H | $CH_3$ | 4-F—benzyl | $CH_3$ | $CH_3$ | O | Br | 194 |
| 20 | 4-t-Bu | H | H | $CH_3$ | 4-Cl—benzyl | $CH_3$ | $CH_3$ | O | Br | 187 |
| 21 | 4-t-Bu | H | H | $CH_3$ | allyl | $CH_3$ | $CH_3$ | O | Br | 94 |
| 22 | 2-Cl | 4-Cl | H | CH(CH$_3$)$_2$ | allyl | H | H | — | Br | 123 |
| 23 | 2-Cl | 4-Cl | H | n-propyl | allyl | H | H | — | Br | oil |
| 24 | 2-Cl | 4-Cl | 6-Cl | H | allyl | H | H | — | Br | 115 |
| 25 | 4-Br | H | H | H | allyl | H | H | — | Br | 126 |
| 26 | 4-Cl | H | H | $CH_3$ | allyl | H | H | — | Br | resin |
| 27 | 2-F | H | H | $CH_3$ | allyl | H | H | — | Br | resin |
| 28 | 2-Cl | 4-Cl | H | $CH_3$ | allyl | H | H | — | Br | resin |
| 29 | 4-acetyl | H | H | $CH_3$ | allyl | H | H | — | Br | resin |
| 30 | 2-Cl | 4-Cl | H | $CH_3$ | $CH_3$ | H | H | — | Br | resin |
| 31 | 2-Cl | 4-Cl | H | $CH_3$ | crotyl | H | H | — | Br | resin |
| 32 | 4-t-Bu | H | H | $CH_3$ | allyl | H | H | — | Br | 125 |
| 33 | 4-Cl | H | H | H | allyl | H | H | — | Br | 89 |
| 34 | 4-Cl | H | H | $CH_3$ | allyl | H | H | $(CH_2)_2$ | Br | 77 |

-continued

| | | | | | | | | | | |
|---|---|---|---|---|---|---|---|---|---|---|
| 35 | 4-Cl | H | H | CH₃ | allyl | H | H | CH₂ | Br | resin |
| 36 | 2-Cl | 4-Cl | 6-Cl | H | benzyl | H | H | — | Br | 156 |
| 37 | 4-t-Bu | H | H | CH₃ | 4-Br—benzyl | CH₃ | CH₃ cis-Dimethyl-morpholine | O | Br | 182 |
| 38 | 2-Cl | 4-Cl | H | CH₃ | CH₃ | H | H | (CH₂)₂ | Br | 178 |
| 39 | 2-Cl | 4-Cl | H | CH₃ | C₂H₅ | H | H | (CH₂)₂ | Br | 178 |
| 40 | 2-Cl | 4-Cl | H | CH₃ | allyl | H | H | (CH₂)₂ | Br | 180 |
| 41 | 4-t-Bu | H | H | CH₃ | 3-Cl—benzyl | CH₃ | CH₃ cis-Dimethyl-morpholine | O | Br | 192 |
| 42 | 4-Cl | H | H | n-butyl | allyl | H | H | — | Br | resin |
| 43 | 4-Br | H | H | CH₃ | allyl | H | H | — | Br | resin |
| 44 | 2-Cl | 4-Cl | H | OCH₃ | allyl | H | H | — | Br | resin |
| 45 | H | H | H | CH₃ | allyl | H | H | — | Br | resin |
| 46 | 4-t-Bu | H | H | CH₃ | 4-Cl—benzyl | H | H | (CH₂)₇ | Br | 169 |
| 47 | 4-t-Bu | H | H | CH₃ | 4-Cl—benzyl | H | H | CH₂ | Br | 117 |
| 48 | 3-Cl | 4-Cl | H | CH₃ | allyl | H | H | — | Br | resin |
| 49 | 4-CH₃ | H | H | CH₃ | allyl | H | H | — | Br | resin |
| 50 | 2-Cl | H | H | CH₃ | allyl | H | H | — | Br | 105 |
| 51 | 3-CH₃ | H | H | CH₃ | allyl | H | H | — | Br | 72 |
| 52 | 2-CH₃ | H | H | CH₃ | allyl | H | H | — | Br | resin |
| 53 | 2-Cl | 4-Cl | H | (CH₃)₂ | allyl | H | H | — | Br | 138 |
| 54 | 3-CH₃ | 4-Cl | H | CH₃ | allyl | H | H | — | Br | resin |
| 55 | 4-Cl | H | H | CH₃ | allyl | H | H | — | Br | 147 |
| 56 | 2-Cl | 4-Cl | H | CH₃ | allyl crotyl | H | H | — | Br | 174 |
| 57 | 2-Cl | 4-Cl | H | CH₃ | crotyl | H | H | — | Br | 128 |
| 58 | 2-Cl | 4-Cl | H | n-propyl | allyl | H | H | CH₂ | Br | resin |
| 59 | 1,1-dimethyl-pentyl | 2-Cl | 6-Cl | CH₃ | allyl | H | H | — | Br | 127 |
| 60 | 2-Cl | 3-Cl | 4-Cl | n-butyl | allyl | H | H | — | Br | resin |
| 61 | 1,1-dimethyl-pentyl | 2-Br | H | CH₃ | CH₃ | CH₃ | CH₃ cis-dimethyl-morpholine | O | Br | resin |
| 62 | 1,1-dimethyl-pentyl | H | H | CH₃ | CH₃ | CH₃ | CH₃ cis-dimethyl-morpholine | O | Br | 149 |
| 63 | 1,1-dimethyl-pentyl | 2-Cl | H | CH₃ | CH₃ | CH₃ | CH₃ cis-dimethyl-morpholine | O | Br | resin |
| 64 | 1,1-dimethyl-butyl | 2-Cl | H | CH₃ | CH₃ | CH₃ | CH₃ cis-dimethyl-morpholine | O | Br | resin |
| 65 | 4-[1-4-t-Bu-phenyl)-prop-2-yl] | H | H | CH₃ | CH₃ | CH₃ | CH₃ cis-dimethyl-morpholine | O | Br | 210 |
| 66 | 4-(1,1-di-ethyl)-ethyl | H | H | CH₃ | CH₃ | CH₃ | CH₃ cis-dimethyl-morpholine | O | Br | 198 |
| 67 | 4-cyclohexyl | 2-Cl | 6-Cl | CH₃ | CH₃ | H | H | — | Br | 159 |
| 68 | 4-t-Bu | 2-Cl | 6-Cl | CH₃ | CH₃ | H | H | CH₂ | Br | resin |
| 69 | 4-t-amyl | 2-Cl | 6-Cl | CH₃ | CH₃ | H | H | — | Br | 189 |
| 70 | 1,1-dimethyl-pentyl | 2-Cl | 6-Cl | CH₃ | 4-Cl—benzyl | H | H | — | Br | 190 |
| 71 | 1,1-dimethyl-butyl | 2-Cl | H | CH₃ | allyl | H | H | — | Br | resin |
| 73 | 1,1-dimethyl-butyl | 2-Cl | H | CH₃ | CH₃ | H | H | — | Br | 138 |
| 74 | 4-CH₃ | 2-Cl | 6-Cl | CH₃ | CH₃ | H | H | CH₂ | Br | 170 |
| 75 | 1,1-dimethyl-pentyl | 2-Cl | 6-Cl | CH₃ | CH₃ | H | H | CH₂ | Br | 180 |
| 76 | 1,1-dimethyl-pentyl | 2-Cl | 6-Cl | CH₃ | propargyl | H | H | CH₂ | Br | 70 |
| 77 | 1,1-dimethyl-pentyl | 2-Cl | 6-Cl | CH₃ | CH₃ | CH₃ | CH₃ | CH₂ | Br | 120 |
| 78 | 1,1-dimethyl-pentyl | 2-Br | H | H | CH₃ | H | H | CH₂ | Br | 178 |
| 79 | 1,1-dimethyl-pentyl | 2-Cl | 6-Cl | CH₃ | CH₃ | H | H | — | Br | 123 |
| 80 | 1,1-dimethyl-pentyl | 2-Cl | 6-Cl | CH₃ | CH₃ | H | H | (CH₂)₂ | Br | 138 |
| 81 | 1,1-dimethyl-pentyl | 2-Cl | 6-Cl | CH₃ | crotyl | H | H | CH₂ | Br | 136 |
| 82 | 1,1-dimethyl-pentyl | 2-Cl | 6-Cl | CH₃ | propargyl | H | H | — | Br | 71 |
| 83 | 1,1-dimethyl-pentyl | 2-Cl | 6-Cl | CH₃ | crotyl | H | H | — | Br | 107 |
| 84 | 1,1-dimethyl-pentyl | 2-Cl | 6-Cl | CH₃ | CH₃ | H | H | — | J | resin |
| 85 | 1,1-dimethyl-pentyl | 2-Cl | 6-Cl | CH₃ | allyl | H | H | CH₂ | Br | 131 |

| No. | R¹ | R² | R³ | R⁴ | R⁵ | R⁶ | R⁷ | (X)$_n$ | Y | M.p. °C |
|---|---|---|---|---|---|---|---|---|---|---|
| 86 | 1,1-dimethyl-pentyl | 2-Cl | 6-Cl | CH₃ | 4-CF₃—benzyl | H | H | CH₂ | Br | 204 |
| 87 | 4-CH₃ | 2-Cl | 6-Cl | CH₃ | allyl | H | H | CH₂ | Br | 145 |
| 88 | 3-CH₃ | H | H | CH₃ | propargyl | H | H | — | Br | 110 |
| 89 | 4-t-Bu | 2-CH₃ | H | CH₃ | allyl | H | H | — | Br | resin |
| 91 | 4-(2-chloro-1,1-dimethyl-ethyl) | H | H | CH₃ | CH₃ | CH₃ cis-dimethyl-morpholine | CH₃ | O | Br | resin |
| 92 | 4-CF₃ | H | H | CH₃ | allyl | H | H | — | Br | resin |
| 93 | 2-CF₃ | H | H | CH₃ | allyl | H | H | — | Br | 118 |
| 94 | 3-CF₃ | H | H | CH₃ | allyl | H | H | — | Br | 124 |
| 95 | 2-Cl | 4-Cl | 6-Cl | H | allyl | H | H | — | Br | resin |
| 96 | 4-t-Bu | 2-CH₃ | H | CH₃ | benzyl | H | H | — | Br | 125 |
| 97 | 4-(1,1-diethyl)-ethyl) | H | H | CH₃ | 4-Cl—benzyl | H | OH | CH₂ | Cl | 92 |

The compounds below may be prepared in a corresponding manner:

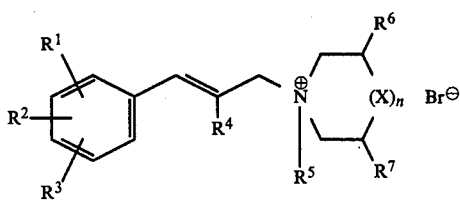

| No. | R¹ | R² | R³ | R⁴ | R⁵ | R⁶ | R⁷ | (X)$_n$ | Y | M.p. °C |
|---|---|---|---|---|---|---|---|---|---|---|
| 5a | 2-Cl | 3-Cl | 4-Cl | n-butyl | allyl | H | H | — | Br | |
| 6a | 2-Cl | 3-Cl | 4-Cl | n-butyl | CH₃ | H | H | — | Br | |
| 7a | 2-Cl | 3-Cl | 4-Cl | n-butyl | 4-Cl—benzyl | H | H | — | Br | |
| 8a | 2-Cl | 3-Cl | 4-Cl | n-propyl | allyl | H | H | — | Br | |
| 9a | 2-Cl | 3-Cl | 4-Cl | n-propyl | CH₃ | H | H | — | Br | |
| 10a | 2-Cl | 3-Cl | 4-Cl | n-propyl | 4-Cl—benzyl | H | H | — | Br | |
| 11a | 4-iso-propyl | H | H | CH₃ | CH₃ | H | H | — | Br | |

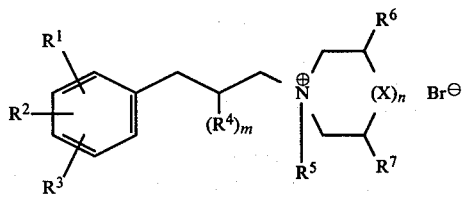

| No. | R¹ | R² | R³ | (R⁴)$_m$ | R⁵ | R⁶ | R⁷ | (X)$_n$ | Y | M.p. °C |
|---|---|---|---|---|---|---|---|---|---|---|
| 72 | 1,1-dimethylpentyl | 2-Cl | 6-Cl | CH₃ | 4-Cl—benzyl | H | H | CH₂ | Br | |
| 90 | C₆H₅ | H | H | CH₃ | CH₃ | CH₃ | CH₃ | O | Br | |

The active ingredients have a strong action on microorganisms. They are particularly suitable for preventing and curing plant diseases caused by fungi such as *Botrytis cinerea* in grapes and strawberries, *Monilia fructigena* in apples, *Phytophothora infestans* in potatoes and tomatoes, *Plasmopara viticola* in grapes, *Alternaria solani* in tomatoes, *Erysiphe graminis* in cereals, and *Erysiphe cichoriacearum* in Cucurbitaceae. They also have a good action on wood-discoloring and wood-destroying fungi such as *Chaetomium globosum, Pullularia pullulans, Sclerophoma pityophila, Aspergillus niger, Coniophora puteana* and *Polystictus versicolor*. The active ingredients also have an advantageous bactericidal action for example on *Staphylococcus aureaus, Escherichia coli,* and *Xanthomonas* and *Pseudomonas* species.

Some of the active ingredients may also be used for combating fungi causing diseases in human beings, e.g., *Trichophyton mentacrophytes* and *Candida albicans*.

The fungicidal or bactericidal agents contain from 0.1 to 95, and preferably from 0.5 to 90, wt.% of active ingredient. Application rates depend on the effect desired, and range from 0.1 to 5 kg of active ingredient per hectare.

The agents according to the invention may also be mixed and applied with other active ingredients, e.g., herbicides, insecticides, growth regulators, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:

manganese N,N-ethylene-bis-dithiocarbamate, manganese zinc N,N-ethylenediamine-bis-dithiocarbamate, the ammonia complex of zinc N,N-ethylene-bis-dithiocarbamate and N,N-polyethylene-bis-(thiocarbamoyl)-disulfide, N-trichloromethylthiotetrahydrophthalimide, N-trichloromethylthio-phthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

However, the compounds according to the invention may also be combined with the following fungicides: dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N-propylene-bis-dithiocarbamate, and the ammonia complex of zinc N,N-propylene-bis-dithiocarbamate and N,N'-polypropylene-bis-(thiocarbamoyl)-disulfide, nitro derivatives, e.g. dinitro-(1-methylheptyl)-phenyl crotonate, 2-sec.-butyl-4,6-dinitrophenyl, 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithioanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, alpha-(2-chloro-phenyl)-alpha-(4-chlorophenyl)-5-pyrimidine-methanol, 1-(4-chlorophenoxy)-3,3-dimethyl-1-(1H-1,2,4-triazol-1-yl)-2-butanone, and 1-(4-chlorophenoxy)-3,3-dimethyl-1-(1H-1,2,4-triazol-1-yl)-2-butanol.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of formulations are given below.

I. 90 parts by weight of compound 9 is mixed with 10 parts by weight of N-methyl-alpha-pyrrolidone. A mixture is obtained which is suitable for application in the form of very fine drops.

II. 20 parts by weight of compound 10 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 12 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound 21 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 23 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 5 parts by weight of compound 25 is intimately mixed with 95 parts by weight of particulate kaolin. A dust is obtained containing 5% by weight of the active ingredient.

VII. 30 parts by weight of compound 28 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 30 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound 31 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following examples demonstrate the biological action of the novel compounds. The prior art active ingredient N-trichloromethylthiotetrahydrophthalimide (A) was used for comparison purposes.

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity to obtain optimum conditions for promoting fungus growth. After 5 days, the disease had spread to such a great extent on the untreated plants that the necroses covered the major portion of the leaves.

The results show that for example active ingredients 59, 63, 69, 70, 72, 75, 76, 77, 78, 79, 80, 81, 82, 83 and 84, applied as 0.05% sprays, had a better fungicidal action (e.g., 97%) than prior art compound A (e.g., 70%).

EXPERIMENT 2

Action on *Phytophthora infestans* in tomatoes

Leaves of potted tomatoes of the "Grobe Fleischtomate" variety were sprayed with aqueous suspensions containing (dry basis) 80% of active ingredient and 20% of emulsifier. After the sprayed-on layer had dried, the leaves were infected with a zoospore suspension of *Phytophthora infestans*. The plants were then place for 5 days in a steam-saturated chamber kept at 16° to 18° C. After this period, the disease had spread on the untreated control plants to such an extent that the fungicidal action of the compounds was able to be assessed.

In this test, for example active ingredients 59, 72, 75, 80, 81, 83 and 84, applied as 0.025% sprays, had a better fungicidal action (e.g., 97%) than prior art compound A (e.g., 60%).

EXPERIMENT 3

Action on wheat mildew

Leaves of pot-grown wheat seedlings of the "Jubilar" variety were sprayed with aqueous emulsions, the solids of which consisted of 80% of active ingredient and 20% of emulsifier, and dusted, after the sprayed-on layer had dried, with spores of wheat mildew (Erysiphe graminis var. tritici). The plants were than placed in a greenhouse at 20° to 22° C. and 75 to 80% relative humidity. The extent of mildew spread was determined after 7 days.

In this experiments, for example active ingredients 9, 10, 12, 21, 23, 25, 28, 30, 31, 32, 34, 37, 38, 39, 41, 43, 46, 47, 53, 71 and 73, applied as 0.025% sprays, had a very good fungicidal action (e.g., 100%).

We claim:

1. A process for combating fungi, wherein the fungi or the plants, areas or seed to be protected against fungus attack are treated with a fungicidal amount of a compound of the formula

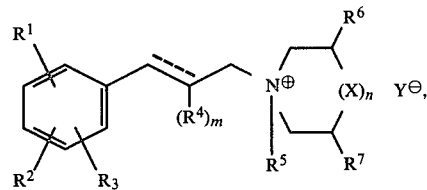

where $R^1$, $R^2$ and $R^3$ independently of one another are each hydrogen, $C_1$–$C_8$ alkyl, $C_1$–$C_4$ haloalkyl, $C_3$–$C_7$ cycloalkyl, phenyl, halophenyl, $C_1$–$C_4$-alkylphenyl, benzyl, halobenzyl, 2,4,6-trimethylbenzyl, phenylethyl, 4-chlorophenylethyl, 4-tert.-butylphenylethyl, 2-phenylpropyl, 2-(p-tert.-butylphenyl)-propyl, 2-(4-chlorophenyl)-propyl, 2-(2,4-dichlorophenyl)propyl, $C_1$–$C_4$-alkoxy, $C_2$–$C_4$-alkanoyl, benzoyl, fluorine, chlorine, bromine or iodine, $R^4$ is, $C_1$–$C_6$-alkyl, $C_3$–$C_4$-alkenyl, or $C_1$–$C_3$-alkoxy, $R^5$ is $C_1$–$C_4$-alkyl, $C_2$–$C_4$-alkenyl, propargyl, benzyl, halobenzyl, 4-cyanobenzyl, 4-nitrobenzyl, 4-$CF_3$-benzyl, or $C_1$–$C_4$-alkylbenzyl, $R^6$ and $R^7$ independently of one another are each hydrogen, alkyl of 1–3 carbons, $CH_2OH$ OR OH, X is $CH_2$, O, S, C=O, $(CH_2)_2$ or $CH_2CH$—$R^8$ where $R^8$ is lower alkyl, m is 0, 1 or 2, n=0 or 1 and $Y^\ominus$ is the anion of a non-phytotoxic acid, with the proviso that the bond represented by the broken line may be hydrogenated if m is 0 or 1, and is always hydrogenated if m is 2.

* * * * *